United States Patent [19]

Nesvadba

[11] Patent Number: 5,618,871
[45] Date of Patent: Apr. 8, 1997

[54] PHENYL PHOSPHITES FOR USE AS STABILIZERS FOR ORGANIC MATERIALS

[75] Inventor: Peter Nesvadba, Marly, Switzerland

[73] Assignee: Ciba-Geigy Corporation, Tarrytown, N.Y.

[21] Appl. No.: 383,277

[22] Filed: Feb. 3, 1995

Related U.S. Application Data

[62] Division of Ser. No. 138,533, Oct. 15, 1993, Pat. No. 5,414,033.

[30] Foreign Application Priority Data

Oct. 21, 1992 [CH] Switzerland ............................ 3262/92

[51] Int. Cl.$^6$ ............................ C08K 5/13; C07C 39/23
[52] U.S. Cl. ............................ 524/326; 568/743
[58] Field of Search ............................ 568/743; 524/348, 524/349, 351, 326

[56] References Cited

U.S. PATENT DOCUMENTS

| | | | |
|---|---|---|---|
| 1,809,204 | 6/1931 | Korten ............................ | 568/743 |
| 2,332,867 | 10/1943 | Niederl ............................ | 568/743 X |
| 2,847,443 | 8/1958 | Hechenbleikner et al. . | |
| 3,127,369 | 3/1964 | Warren . | |
| 3,281,381 | 10/1966 | Hechenbleikner et al. . | |
| 3,310,609 | 3/1967 | Baranauckas et al. . | |
| 3,509,091 | 4/1970 | Cleveland et al. . | |
| 3,812,219 | 5/1974 | Clovis et al. . | |
| 4,013,708 | 3/1977 | Haas et al. ............................ | 560/59 |
| 4,054,669 | 10/1977 | Lahourcade et al. ............ | 568/743 X |
| 4,325,863 | 4/1982 | Hinsken et al. . | |
| 4,338,244 | 7/1982 | Hinsken et al. . | |
| 4,677,184 | 6/1987 | Mark ............................ | 528/198 |
| 4,691,042 | 9/1987 | Mendoza et al. ............ | 560/61 |
| 4,739,090 | 4/1988 | Tajima et al. . | |
| 4,810,814 | 3/1989 | Morgan ............................ | 558/335 |
| 4,873,376 | 10/1989 | Dujardin et al. ............ | 568/806 |
| 5,175,312 | 12/1992 | Dubs et al. . | |

FOREIGN PATENT DOCUMENTS

| | | |
|---|---|---|
| 0048878 | 4/1982 | European Pat. Off. . |
| 0356688 | 3/1990 | European Pat. Off. . |
| 2027713 | 2/1980 | United Kingdom . |

OTHER PUBLICATIONS

Database Beilstein on STN, Beilstein Informationssysteme GmbH, (Frankfurt, Germany), Beilstein Reference No. 3–06–00–02751, Boettcher, F., Diss. (Univ. Berlin 1930) S. 57 1930.
R. Gächter et al., Plastics Additives Handbook 3rd Ed. p. 47 (1990).
Houben – Weyl, vol. E1, pp. 373–376, Georg Thieme Verlag, Stuttgart (1982).
Houben – Weyl, 2nd Ed, vol. X11/2 p. 48, Georg Thieme Verlag, Stuttgart (1964).
W.D. Wulff, et al., J. Amer. Chem. Soc. 106, 1132 (1984).
Ullmanns Enzyklopadie der Technischen Chemie, vol. 13, pp. 85–94, Verlag Chemie Weinheim (1977).

Primary Examiner—Johann Richter
Assistant Examiner—Michael G. Ambrose
Attorney, Agent, or Firm—Michele A. Kovaleski

[57] ABSTRACT

Novel compounds of the formula I and formula II

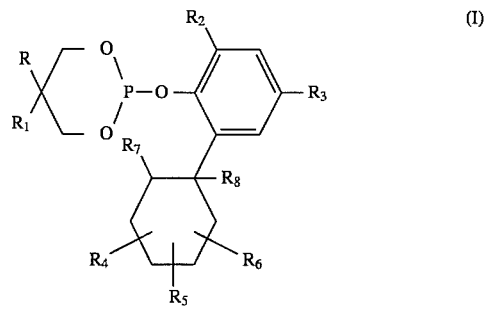

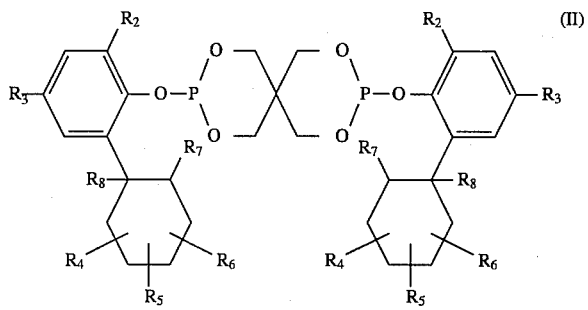

in which

R and $R_1$, independently of one another, are hydrogen or $C_1$–$C_4$alkyl or together with the carbon atom to which they are attached form a 3,4-dehydrocyclohexylidene ring, $R_2$ is hydrogen, $C_1$–$C_8$alkyl or $C_5$–$C_6$cycloalkyl, $R_3$ is $C_1$–$C_8$alkyl or $C_{5–C6}$cycloalkyl, $R_4$, $R_5$ and $R_6$, independently of one another, are hydrogen or $C_{1–C4}$alkyl, $R_4$, $R_5$ and $R_6$ together containing 1 to 4 carbon atoms, and $R_7$ and $R_8$ are hydrogen or together an additional direct bond, are described for use as stabilizers for organic materials against thermal, oxidative or light-induced degradation.

5 Claims, No Drawings

PHENYL PHOSPHITES FOR USE AS STABILIZERS FOR ORGANIC MATERIALS

This is a divisional of Ser. No. 08/138,533, filed Oct. 15, 1993, now U.S. Pat. No. 5,414,033.

The present invention relates to novel phenyl phosphites, compositions comprising an organic material, preferably a polymer, and the novel phenyl phosphites, and to the use thereof for stabilizing organic materials against oxidative, thermal or light-induced degradation.

Organic phosphites are known in the art as co-stabilizers, secondary antioxidants and processing stabilizers for polyolefins and the like; examples of such known phosphite stabilizers can be found in R. Gächter/H. Müller (ed.), Plastics Additives Handbook, 3rd Ed., p. 47, Hanser, Munich 1990, and in EP-A-356 688.

There is a continued need for effective stabilizers for organic materials which are sensitive to oxidative, thermal or light-induced degradation.

It has now been found that a selected group of such phosphites are surprisingly particularly suitable for use as stabilizers for organic materials which are sensitive to oxidative, thermal or light-induced degradation. The usefulness of the compounds mentioned for use as processing stabilizers for synthetic polymers should be mentioned in particular.

Accordingly, the present invention relates to compounds of the formula I or II in which R and $R_1$, independently of one another, are hydrogen or $C_1$–$C_4$alkyl or together with the carbon atom to which they are attached form a 3,4-dehydrocyclohexylidene ring, $R_2$ is hydrogen, $C_1$–$C_8$alkyl or $C_5$–$C_6$cycloalkyl, $R_3$ is $C_1$–$C_8$alkyl or $C_5$–$C_6$cycloalkyl, $R_4$, $R_5$ and $R_6$, independently of one another, are hydrogen or $C_1$–$C_4$alkyl, $R_4$, $R_5$ and $R_6$ together containing 1 to 4 carbon atoms, and $R_7$ and $R_8$ are hydrogen or together form an additional direct bond.

Alkyl having up to 8 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl or 2-ethylhexyl. For R and $R_1$ methyl is preferred, and for $R_2$ and $R_3$, tert-butyl is preferred. The 3,4-dehydrocyclohexylidene ring is Examples of $C_5$–$C_6$cycloalkyl are cyclopentyl or cyclohexyl.

In the case where $R_4$, $R_5$ and $R_6$, independently of one another, are hydrogen or $C_1$–$C_4$-alkyl and $R_4$, $R_5$ and $R_6$ together contain 1 to 4 carbon atom, they are, for example, the following cyclohexen-1-yl substituents on the phenyl radicals in the general formulae I or II:

Preference is given to compounds of the formula I or II in which $R_2$ is hydrogen or $C_1$–$C_4$alkyl, $R_3$ is $C_1$–$C_4$alkyl, $R_4$, $R_5$ and $R_6$ are hydrogen, and $R_7$ and $R_8$ together form an additional direct bond.

Particular preference is given to compounds of the formula I or II in which R and $R_1$ are methyl, $R_2$ and $R_3$ are $C_1$–$C_4$alkyl, and $R_4$, $R_5$ and $R_6$ are hydrogen.

Of particular interest are compounds of the formula I or II in which $R_7$ and $R_8$ together form an additional direct bond.

The compounds of the formula I and formula II according to the invention can be prepared in a manner known per se.

For example, this being preferred, a phenol of the formula III

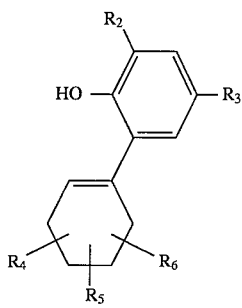

(III)

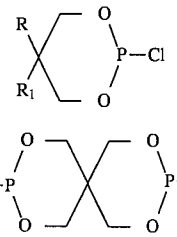

(IV)

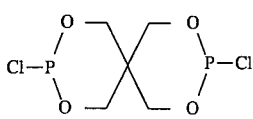

(V)

is reacted with a chlorophosphite of the formula IV or V in the presence of a suitable organic, polar or apolar, aprotic solvent This reaction is preferably carried out in the presence of a base at temperatures of between −20° C. and the boiling point of the solvent.

The base can be used in different mounts, ranging from catalytic via stoichiometric amounts up to a manifold molar excess relative to the phenol or chlorophosphite used. In some cases, the hydrogen chloride formed in the reaction is converted by the base into chloride, which can be removed by filtration and/or washing with a suitable aqueous or solid phase, during which a second, water-immiscible solvent can also be used. Purification of the product is advantageously carried out by recrystallization of the residue from the organic phase obtained after concentration or evaporation to dryness.

Suitable solvents for carrying out the reaction are, inter alia, hydrocarbons (for example mesitylene, toluene, xylene, hexane, pentane or further petroleum ether fractions), halogenated hydrocarbons (for example di- or trichloromethane, 1,2-dichloroethane, 1,1,1-trichloroethane), ethers (for example diethyl ether, dibutyl ether or tetrahydrofuran), further-more acetonitrile, dimethylformamide, dimethyl surfoxide or N-methylpyrrolidone.

Suitable bases are, inter alia, tertiary mines (for example trimethylamine, triethylamine, tributylamine, N,N-dimethylaniline, N,N-diethylaniline or pyridine), hydrides (for example lithium hydride, sodium hydride, potassium hydride) or alcoholates (for example sodium methoxide).

Hydrides (for example sodium hydride, sodium borohydride or lithium aluminium hydride), alkali metals, alkali metal hydroxides or sodium methoxide can also be used for obtaining the phenolate of the formula III; the reaction product which may be formed during this reaction (for example water, methanol) is distilled off (for example as an azeotrope with toluene) before reaction with the chlorophosphite of the formula IV or V takes place.

The preparation of the chlorophosphites of the formula IV and V is known and described, for example, in Houben-Weyl, volume E1, page 373–376, Georg Thieme Verlag, Stuttgart, 1982, and Houben-Weyl, 2nd edition, volume XII/2, page 48, Georg Thieme Verlag, Stuttgart, 1964.

The compounds of the formula I and formula II according to the invention in which $R_7$ and $R_8$ together form an additional direct bond can be reacted, for example, by catalytic hydrogenation in accordance with Organikum (Preparative Organic Chemistry), pages 288–298, Deutscher Verlag der Wissenschaften Berlin 1986, in an organic solvent in a temperature range from, for example 0° to 100° C. and, if desired, under a slight pressure to give the compounds of the formula I and II according to the invention in which $R_7$ and $R_8$ are hydrogen. Catalysts which are preferably used are palladium on carbon, platinum oxide or Raney nickel. Suitable organic solvents, which may also contain water, are in particular alcohols, for example methanol, ethanol or isopropanol, and tetrahydrofuran, dioxane, ethyl acetate, toluene or dimethylacetamide.

The compounds of the formula I and formula II according to the invention in which $R_7$ and $R_8$ are hydrogen can also be prepared from the hydrogenated phenol of the formula IIIa

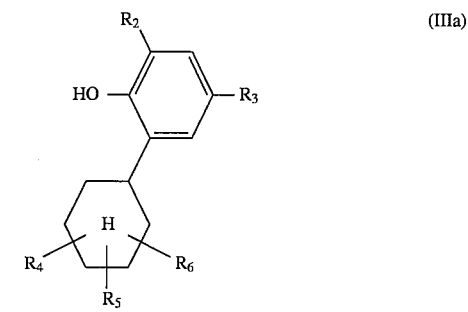

(IIIa)

as the starting material, which, for example, is prepared from the phenol of the formula III by catalytic hydrogenation of the double bond using the abovementioned reaction conditions, by reaction with a chlorophosphite of the formula IV or V using the abovementioned reaction conditions in the presence of a suitable organic, polar or apolar solvent.

The phenols of the formula III are mostly unknown in the literature. Only the compound of the formula VI has been prepared, by W. D. Wulff et al, J. Amer. Chem. Soc. 106, 1132 (1984) in a complicated manner.

Accordingly, the present invention also provides compounds of the formula III

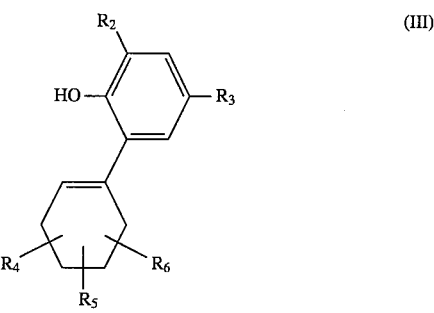

(III)

in which $R_2$ is hydrogen, $C_1$–$C_8$alkyl or $C_5$–$C_6$cycloalkyl, $R_3$ is $C_1$–$C_8$alkyl or $C_5$–$C_6$cycloalkyl, $R_4$, $R_5$ and $R_6$, independently of one another, are hydrogen or $C_1$–$C_4$alkyl, $R_4$, $R_5$ and $R_6$ together containing 1 to 4 carbon atoms, on condition that the compound of the formula VI is excluded.

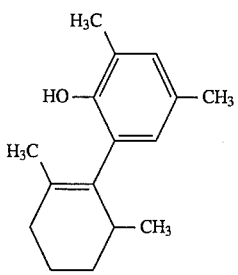

Preference is given to compounds of the formula III in which

R$_2$ is hydrogen or C$_1$–C$_4$alkyl,

R$_3$ is C$_1$–C$_4$alkyl, and

R$_4$, R$_5$ and R$_6$ are hydrogen.

Particular preference is given to compounds of the formula III in which R$_2$ is tert-butyl.

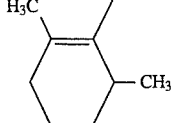

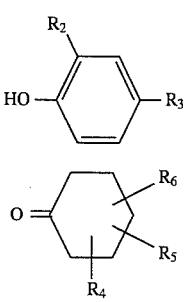

The compounds of the formula III are prepared, for example, this being preferred, by condensation of the phenols of the formula VII, which are unsubstituted in at least one ortho position, with cyclohexanones of the formula VIII. The reaction is carried out at elevated temperature, in particular temperatures of 20° to 100° C., in the melt or in a solvent, where appropriate under slight pressure. The reaction is preferably carried out in the melt in a temperature range from 20° to 80° C., in particular 40° to 60° C. The reaction can be catalyze by addition of an acid, such as hydrochloric acid, sulfuric acid or methanesulfonic acid. Preferably, hydrogen chloride gas is used.

The compounds of the formula I and formula II according to the invention are highly suitable for stabilizing organic materials against oxidative, thermal or light-induced degradation. The compounds of the formula III are also suitable for stabilizing organic materials against oxidative, thermal or light-induced degradation.

Examples of such organic materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated, magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures there of with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/-isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPF/EAA and alternating or random polyalkylene/carbon monoxide copolymers and mixtures thereof with other polymers, for example polyamides.

4. Hydrocarbon resins (for example C$_5$–C$_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated robbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha$, $\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides-and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, robber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic robber, e.g. natural latex or latices of carboxylated styrene/butadiene copolymers.

Accordingly, the invention also relates to compositions comprising (a) an organic material subjected to oxidative, thermal or light-induced degradation and (b) at least one compound of the formula I or formula II.

The invention also relates to a composition comprising (a) an organic material subjected to oxidative, thermal or light-induced degradation and (b) at least one compound of the formula III.

Preferably, the, organic materials to be protected are natural, semi-synthetic or, preferably, synthetic organic materials. Particular preference is given to thermoplastic polymers, in particular PVC or polyolefins, especially polyethylene and polypropylene.

The action of the compounds according to the invention against thermal and oxidative degradation, especially under thermal stress, such as occurs during processing of thermoplastics, may be mentioned in particular. Accordingly, the compounds according to the invention are highly suitable for use as processing stabilizers.

Preferably, the compounds of the formula I or formula II are added to the material to be stabilized in amounts of 0.01 to 10%, for example 0.01 to 5%, preferably 0.05 to 3%, in particular 0.05 to 1%, relative to the weight of the organic material to be stabilized.

The compositions according to the invention can contain, in addition to the compounds of the formula I or formula II, further co-stabilizers, for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-di-methyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-di-phenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis (6-tert-butyl-2-methylphenol), 4,4'-thiobis-(3,6-di-sec-amylphenol), 4,4'-bis-(2,6-dim-ethyl-4-hydroxyphenyl) disulfide.

1.5. Alkylidenebisphenols, for example 2,2'-methylenebis(6-tert-butyl-4-methylphenol), 2,2 '-methylenebis(6-tert-butyl-4-ethylphenol), 2,2'-methylenebis [4-methyl-6-(α-methylcyclohexyl)phenol], 2,2'-methylenebis(4-methyl-6-cyclohexylphenol), 2,2'-methylenebis (6-nonyl-4-methylphenol), 2,2'-methylenebis(4,6-di-tert-butylphenol), 2,2'-ethylidenebis (4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2, 6-di-tert-butylphenol), 4,4'-methylenebis (6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris (5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3, 5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5-dicyclohexyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and Light Stabilisers 2.1.2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotrizole,2-(5'-tert-butyl-2'-hydroxyphenyl) benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethyl butyl)-6-benzotriazole-2-ylphenol]; the transesterification product of 2-[3'-tert-butyl-5'-(2-methoxycarbon ylethyl)-2'-hydroxyphenyl]-2H-benzotriazole with polyethylene glycol 300; [R—CH$_2$CH$_2$—COO(CH$_2$)$_3$ ]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-pheny-4-lanroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-penta-methylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butyl-amino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopmpyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8.2-(2-Hydroxyphenyl)-1,3,5-triazines, for example 2,4,6-tris (2-hydroxy-4-octyloxyphenyl)-1,3,5-triazine, 2-(2-hydroxy-4-octyloxyphenyl)-4,6-bis(2,4-dimethylphenyl)-1,3,5triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy- 3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylate-N'-salicyloyl hydrazine, N,N'-bis(salicyloyl) hydrazine, N,N'-bis(3,5-di-tert-butyl-4-hydroxyphenylpropionyl) hydrazinc, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioetadecyl phosphite, distearyl pentaerythritol diphosphite, tris(2,4-di-tert-butylphenyl) phosphite, diisodecyl pentaerythritol diphosphite, bis(2,4-di-tert-butylphenyl pentaerythritol diphosphite, bis(2,6-di-tert-butyl-4-methylphenyl)-pentaerythritol hritol diphosphite, diisodecyloxypentaerythriol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetralds(2,4-di-tert-butylphenyl) 4,4'-biphenylene diphosphonite, 6-isooctyl-oxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1, 3,2-dioxaphosphocin, bis(2,4-di-tert-butyl-6-methylphenyl) methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazinc derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other admirers, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863, U.S. Pat. No. 4,338, 244 or U.S. Pat. No. 5,175,312, or 3-[4-(2-acetoxyethoxy) phenyl]-5,7-di-tert-butyl-benzofuran-2-one 5,7-di-tert-butyl-3-[4-(2-stearoyloxyethoxy) phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The co-stabilizers, with the exception of the benzofuranones listed under 11, are added for example in concentrations of 0.01 to 10%, relative to the total weight of the material to be stabilized.

Further preferred compositions further comprise, in addition to component (a) and the compounds of the formula I or formula II, further additives, in particular phenolic antioxidants, light stabilizers or processing stabilisers.

Particularly preferred additives are phenolic antioxidants (item 1 of the list, sterically hindered amines (item 2.6 of the list), phosphites and phosphorrites (item 4 of the list) and peroxide-destroying compounds (item 5.) of the list.

Additional additives (stabilizers) which are also particularly preferred are benzofuran-2ones, such as described, for example, in U.S. Pat. No. 4,325,863, U.S. Pat. No. 4,338, 244 or U.S. Pat. No. 5,175,312.

Examples of such benzofuran-2-ones are compounds of the formula

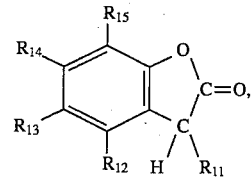

in which $R_{11}$ is phenyl or phenyl which is substituted by 1 to 3 alkyl radicals together having at most 18 carbon atoms, alkoxy having 1 to 12 carbon atoms, alkoxycarbonyl having 2 to 18 carbon atoms or chlorine;

$R_{12}$ is hydrogen;

$R_{14}$ is hydrogen, alkyl having 1 to 12 carbon atoms, cyclopenty, cyclohexyl or chlorine;

$R_{13}$ has the meaning of $R_{12}$ or $R_{14}$ or is a radical of the formula

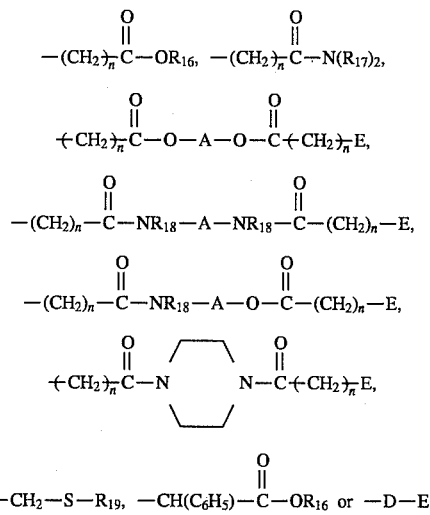

in which $R_{16}$ is hydrogen, alkyl having 1 to 18 carbon atoms, alkyl having 2 to 18 carbon atom which is interrupted by oxygen or sulfur, dialkylaminoalkyl having a total of 3 to 16 carbon atoms, cyclopontyl, cyclohexyl, phenyl or phenyl which is substituted by 1 to 3 alkyl radicals together having at most 18 carbon atoms;

n is 0, 1 or 2;

the substituents $R_{17}$, independently of one another, are hydrogen, alkyl having 1 to 18 carbon atoms, cyclopentyl, cyclohexyl, phenyl, phenyl which is substituted by 1 or 2 alkyl radicals together having at most 16 carbon atoms, a radical of the formula —$C_2H_4OH$, —$C_2H_4$—O—$C_mH_{2m+1}$ or

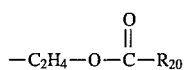

or together with the nitrogen atom to which they are attached form a piperidine or morpholine radical;

m is 1 to 18;

$R_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur;

$R_{18}$ is hydrogen, alkyl having 1 to 18 carbon atoms, cyclopentyl, cyclohexyl, phenyl, phenyl which is substituted by 1 or 2 alkyl radicals together having at most 16 carbon atoms, or is benzyl;

$R_{19}$ is alkyl having 1 to 18 carbon atoms;

D is —O—, —S—, —SO—, —$SO_2$—or—$C(R_{21})_2$—;

the substituents $R_{21}$, independently of one another, are hydrogen, $C_1$–$C_{16}$alkyl, the two $R_{21}$ together containing 1 to 16 carbon atoms, $R_{21}$ is furthermore phenyl or a radical of the formula

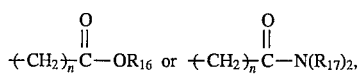

in which n, $R_{16}$ and $R_{17}$ are as defined above;

E is a radical of the formula

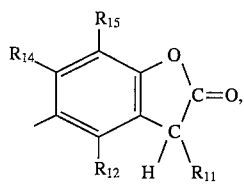

in which $R_{11}$, $R_{12}$ and $R_{14}$ are as defined above; and $R_{15}$ is hydrogen, alkyl having 1 to 20 carbon atoms, cyclopentyl, cyclohexyl, chlorine or a radical of the formula

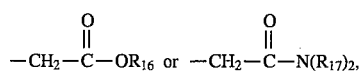

in which $R_{16}$ and $R_{17}$ are as defined above, or $R_{15}$ together with $R_{14}$ forms a tetramethylene radical.

Preference is given to those benzofuran-2-ones in which $R_{13}$ is hydrogen, alkyl having 1 to 12 carbon atoms, cyclopentyl, cyclohexyl, chlorine or a radical of the formula

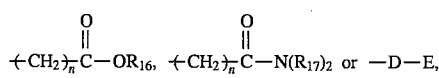

in which n, $R_{16}$, $R_{17}$, D and E are as defined above, $R_{16}$ is in particular hydrogen, alkyl having 1 to 18 carbon atoms, cyclopentyl or cyclohexyl.

Preference is given furthermore to those benzofuran-2-ones in which $R_{11}$ is phenyl or phenyl which is substituted by 1 or 2 alkyl radicals together having at most 12 carbon atoms; $R_{12}$ is hydrogen; $R_{14}$ is hydrogen or alkyl having 1 to 12 carbon atoms; $R_{13}$ is hydrogen, alkyl having 1 to 12 carbon atoms,

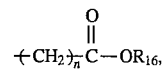

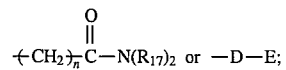

$R_{15}$ is hydrogen, alkyl having 1 to 20 carbon atoms,

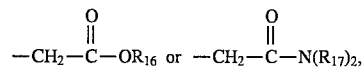

or $R_{15}$ together with $R_{14}$ forms a tetramethylene radical, n, $R_{16}$, $R_{17}$, D and E being as defined at the beginning.

Of particular interest are also those benzofuran-2-ones in which $R_{11}$ is phenyl; $R_{13}$ is hydrogen, alkyl having 1 to 12 carbon atoms or -D-E; $R_{12}$ and $R_{14}$, independently of one another, are hydrogen or alkyl having 1 to 4 carbon atoms; and $R_{15}$ is alkyl having 1 to 20 carbon atoms, D and E being as defined at the beginning.

Of special interest are finally also those benzofuran-2-ones in which $R_{11}$ is phenyl; $R_{13}$ is alkyl having 1 to 4 carbon atoms or-D-E; $R_{12}$ and $R_{14}$ are hydrogen; and $R_{15}$ is alkyl having 1 to 4 carbon atoms, cyclopentyl or cyclohexyl, D being a group —$C(R_{21})_2$- and E being a radical of the formula

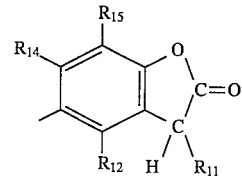

the substituents $R_{21}$ being identical to or different from one another and each being alkyl having 1 to 4 carbon atoms, and $R_{11}$, $R_{12}$, $R_{14}$ and $R_{15}$ being as defined.

The amount of additional additives, in particular stabilisers, for example of the benzofuran-2-ones mentioned, can vary within wide limits. For example, 0.0005 to 10, preferably 0.001 to 5, in particular 0.01 to 2, % by weight thereof can be pregnt in the compositions according to the invention.

Incorporation of the compounds of the formula I or formula II and, if desired, further additives in the polymer organic material is carried out by known methods, for example before or during raoulcling or by applying the dissolved or dispersed compounds to the polymer organic material, if appropriate with subsequent slow evaporation of the solvent. The compounds of the formula I or formula II can also be added to the materials to be stabilized in the form of a masterbatch containing them, for example, in a concentration of 2.5 to 25% by weight.

The compounds of the formula I or formula II can also be added before or during polymerization or before crosslinking.

The compounds of the formula I or formula II can be incorporated in the material to be stabilized in pure form or encapsulated in waxes, oils or polymers.

The compounds of the formula I or formula II can also be sprayed onto the polymer to be stabilized. They are capable of diluting other additives (for example the abovementioned customary additives) or their melts, thus enabling them to be sprayed onto the polymer to be stabilized also together with these additives. Addition by spraying during deactivation of the polymerization catalysts is particularly advantageous, it being possible, for example, for the steam used for deactivation to be used for spraying. In the case of bead polymerized polyolefins, it may be advantageous, for example, to apply the compounds of the formula I or formula II, if desired together with other additives, by spraying.

The materials thus stabilized can be used in a wide range of forms, for example as films, fibres, tapes, moulding compositions, profiles or as binders for paints, adhesives or cements.

As already mentioned, the organic materials to be protected are preferably organic, in particular synthetic, polymers. Of these, the materials being protected are particularly advantageously thermoplastic materials, in particular polyolefins. The excellent efficiency of the compounds of the formula I or formula II as processing stabilizers (thermal stabilizers) should be mentioned in particular. To this end, they are advantageously added to the polymer before or during its proceeding. It is however also possible to stabilize other polymers (for example elastomers) or lubricants or hydraulic fluids against degradation, for example light-induced or thermal-oxidative degradation. For elastomers, see the above list of possible organic materials.

Suitable lubricants and hydraulic fluids are based, for example, on mineral or synthetic oils or mixtures thereof. Lubricants are known to one skilled in the art and described in the relevant technical literature, for example in Dieter Klamann, "Schraierstoffe und verwandie Produkte" (Verlag Chemic, Weinheim 1982), in Schewe-Kobek, "Das Schraier-mittel-Taschenbuch" (Dr. Alfred Hüthig-Veriag, Heidelberg, 1974) and in "Ullmanns Enzyklopädie der technischen Chemic" vol. 13, pages 85–94 (Verlag Chemie, Weinheim, 1977).

Accordingly, a preferred embodiment of the present invention is the use of compounds of the formula I or formula II for stabilizing organic materials against oxidative, thermal or light-induced degradation.

The compounds of the formula I or formula II according to the invention are preferably used as processing stabilizers (thermal stabilizers) of thermoplastic polymers.

The present invention also provides a process for stabilizing an organic material against oxidative, thermal or light-induced degradation, which comprises incorporating therein or applying thereto at least one compound of the formula I or formula II.

The examples which follow further illustrate the invention. The parts or percentages given are by weight.

EXAMPLE 1

Preparation
2,4-di-tert-butyl-6-(cyclohexen-1-yl)phenol
(compound (101), Table 1)

24.75 g (120 mmol) of 2,4-di-tert-butylphenol and 2.95 g (30.0 mmol) of cyclohexanone are melted at 60° C. The melt is then cooled to 45° C., saturated with hydrogen chloride gas, and the mixture is stirred at 45° C. for 24 hours. 50 ml of methanol are added, and the reaction mixture is cooled with ice/water. The precipitated product is filtered and washed with a small amount of cold methanol to give 4.55 g of product. The filtrate is concentrated on a vacuum rotary evaporator, and excess 2,4-di-tert-butylphenol is distilled off in a high vacuum. Crystalization of the residue from 10 ml of methanol gives another 1.75 g of product. Thus, a total of 6.3 g (73%) of 2,4-di-tert-butyl-6-(cylclohexen-1-yl)phenol, m.p. 102°–104° C. (compound(101), Table 1) are obtained.

Analogously to Example 1,6-(eyclohexen-1-yl)-2-tert-butyl-4-methylphenol (102) is prepared from 2-tert-butyl-4-methylphenol as the starting material. Purification of the compound (102) is achieved by chromatography on silica gel using 1:9 diehloromethane/hexane as the eluent system.

TABLE 1

| No. | Compound | m.p. (°C.) | C (%), H (%) (calculated/found) | | Yield (%) |
|---|---|---|---|---|---|
| 101 | 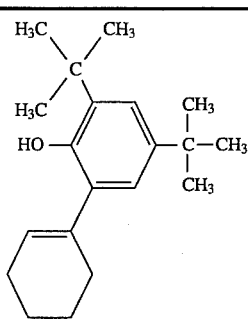 | 102–104 | 83.85<br>83.74 | 10.55<br>10.49 | 73 |
| 102 | 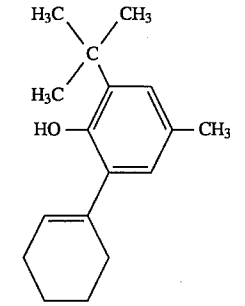 | Oil | 83.55<br>83.44 | 9.90<br>9.99 | 53 |

EXAMPLE 2

Preparation of
2-[6-(cyclohexen-1-yl)-2-tert-butyl-4-methyl-phenoxy]-5,
5dimethyl-1,3,2-dioxaphosphorinane (compound
(201), Table 2)

4.85 g (29.0 mmol) of 2-chloro-5,5-dimethyl-1,3,2-dioxaphosphorinane are added dropwise over a period of about 15 minutes to a solution of 6.6 g (27.0 mmol) of 6-(cyclohexen-1-yl)-2-tert-butyl-4-methylphenol (compound(102), Example 1) and 4.0 ml (29.0 mmol) of triethylamine in 25 ml of mesitylene (1,3,5-trimethylbenzene). The reaction mixture is then refluxed for 18 hours, cooled, filtered, and the filtrate is concentrated on a vacuum rotary evaporator. Crystallization of the residue from dry acetonitrile gives 5.8 g (57%)of 2-[6-(cyclohexen-1-yl)-2-tert-butyl-4-methyl-phenoxy]-5, 5-dimethyl-1,3,2-dioxaphosphorinane, m.p. 97°–102° C. (compound(201), Table 2).

Analogously to Example 2, compound(202)(Table 2) is obtained from 2, 4-di-tert-butyl-6-(cyclohexen-1-yl)phenol (compound(101), Table 1, Example 1) as the starting material. Compound (203)(Table 2) is obtained using two equivalents of 2, 4-di-tert-butyl-6-(cyclohexen-1-yl)phenol and 3,9-dichloro-2,4,8,10-tetraoxa-3,9-diphosphaspiro[5.5]undecane instead of 2-chloro-5,5-dimethyl-1,3,2-dioxaphosphorinane.

TABLE 2

| No. | Compound | m.p. (°C.) | C (%), H (%), P (%) (calculated/found) | | | Yield (%) |
|---|---|---|---|---|---|---|
| 201 | [structure] | 97–102 | 70.19 / 70.21 | 8.84 / 8.88 | | 57 |
| 202 | [structure] | 220–225 | 71.74 / 71.66 | 9.39 / 9.42 | 7.40 / 7.27 | 61 |
| 203 | [structure] | 267–269 | 70.65 / 70.26 | 8.69 / 8.96 | 8.10 / 8.06 | 50 |

EXAMPLE 3

Stabilization of Polypropylene in Multiple Extrusion 1.3 kg of polypropylene powder ((Moplen®FL S20) which has been prestabilzed with 0.015% of Irganox®1076 n-octadecyl (3-[3,5-di-tert-butyl-4-hydroxyphenyl]propionate) (having a melt index of 3.2 as measured at 230° C. and on 2.16 kg) are mixed with 0.05% of Irganox®1010 (pentaerythritol tetrakis-[3-(3,5-di-tert-butyl-4-hydroxyphenyl)-propionate), 0.05% of calcium stearate, 0.03% DHT 4A®(Kyowa Chemical Industry Co., Ltd., [$Mg_{4.5}Al_2(OH)_{13}CO_3 \cdot 3,5H_2O$]) and 0.05% of the compound from Table 2. This mixture is extruded in an extruder having a cylinder diameter of 20 mm and a length of 400 mm at 100 revolutions per minute, 3 heating zones being set at the following temperatures: 260°, 270°, 280° C. For cooling, the extrudate is led through a water bath and then granulated. These granules are repeatedly extruded. After 3 extrusions, the melt index is measured (at 230° C. and on 2.16 kg). A large increase of the melt index indicates extensive chain degradation, i.e., poor stabilization. The results are summarized in Table 3.

TABLE 3

| Compound from Table 2 | Melt index after 3 extrusions |
|---|---|
| — | 15.0 |
| 201 | 2.80 |
| 202 | 2.90 |
| 203 | 2.60 |

EXAMPLE 4

Stabilization of Polyethylene During Processing 100 parts of polyethylene powder (Lupolen®5260Z) are mixed with 0.05 parts of Irganox®1010 (pentaerythritol tetrakis-[3-(3,5-di-tert-butyl-4-hydroxyphenyl)propionate]) and 0.1 part of the stabilizer from Table 2, and the mixture is kneaded in a Brabender plastigraph at 220° C. and 50 revolutions per minute. During this time, the resistance to kneading is continuously recorded as torque. During kneading, the polymer, after remaining constant for an extended period of time, starts crosslinking, which can be detected by the rapid increase in torque. In Table 4, the time until a distinct increase in torque takes place is shown as a measure of the stabilizer effect. The longer this time, the better the stabilizer effect.

TABLE 4

| Compound from Table 2 | Time until torque increases (min.) |
|---|---|
| — | 5.0 |
| 201 | 11.0 |
| 202 | 10.5 |

What is claimed is:

1. A compound of the formula III

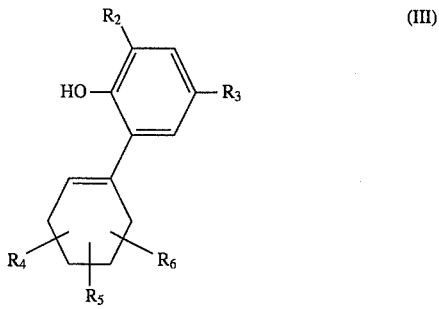

in which $R_2$ is hydrogen, $C_1$–$C_8$alkyl or $C_5$–$C_6$cycloalkyl, $R_3$ is $C_1$–$C_8$ alkyl or $C_5$–$C_6$cycloalkyl, $R_4$, $R_5$ and $R_6$, independently of one another, are hydrogen or $C_1$–$C_4$alkyl, $R_4$, $R_5$ and $R_6$ together containing up to 4 carbon atoms, provided that if $R_2$, $R_4$, $R_5$, and $R_6$ each represent hydrogen, then $R_3$ cannot be methyl, and also on condition that the compound of the formula VI is excluded.

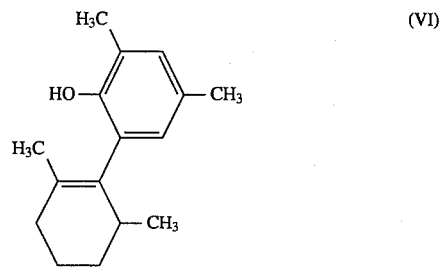

2. A compound according to claim 1, in which
$R_2$ is hydrogen or $C_1$–$C_4$alkyl,
$R_3$ is $C_1$–$C_4$alkyl, and
$R_4$, $R_5$ and $R_6$ are hydrogen.

3. A compound according to claim 1, in which $R_2$ is tert-butyl.

4. A composition comprising
   a) an organic material subjected to oxidative, thermal or light-induced degradation and
   b) at least one compound of the formula III according to claim 1.

5. A composition according to claim 4, comprising, as component a), natural, semi-synthetic or synthetic polymers.

* * * * *